(12) United States Patent
Mueller et al.

(10) Patent No.: US 11,532,144 B2
(45) Date of Patent: Dec. 20, 2022

(54) METHOD AND APPARATUS FOR ACTUATING A MEDICAL IMAGING DEVICE

(71) Applicant: Siemens Healthcare GmbH, Erlangen (DE)

(72) Inventors: Kerstin Mueller, San Francisco, CA (US); Stefan Lautenschlaeger, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 106 days.

(21) Appl. No.: 17/029,257

(22) Filed: Sep. 23, 2020

(65) Prior Publication Data
US 2021/0097322 A1     Apr. 1, 2021

(30) Foreign Application Priority Data

Sep. 30, 2019 (EP) .................................... 19200340

(51) Int. Cl.
*A61B 6/00*     (2006.01)
*G06V 10/25*    (2022.01)
(Continued)

(52) U.S. Cl.
CPC .............. *G06V 10/25* (2022.01); *A61B 6/032* (2013.01); *A61B 6/4405* (2013.01); *A61B 6/469* (2013.01);
(Continued)

(58) Field of Classification Search
CPC .. G06V 10/25; G06V 10/10; G06V 2201/031; A61B 6/032; A61B 6/4405; A61B 6/469; A61B 6/5217; A61B 6/545; A61G 3/001; A61G 2210/50; G06T 7/0012; G06T 11/003; G06T 2200/04; G06T 2207/10081; G06T 2207/20081; G06T 2207/30016
See application file for complete search history.

(56) References Cited

U.S. PATENT DOCUMENTS

2012/0093383 A1    4/2012   Claus
2015/0254837 A1    9/2015   Goyal
(Continued)

OTHER PUBLICATIONS

Extended European Search Report for European Application No. 19200340.8 dated Mar. 24, 2020.

*Primary Examiner* — Siamak Harandi
(74) *Attorney, Agent, or Firm* — Harness, Dickey & Pierce, P.L.C.

(57) ABSTRACT

A method is for actuating a medical imaging device for generating a second three-dimensional image dataset including a target region in a region of interest of a patient with a functional impairment. The method includes providing a first three-dimensional image dataset including the region of interest of the patient; identifying the target region based on the first three-dimensional image dataset, a partial region of the region of interest with the functional impairment being determined; determining an imaging parameter for generating the second three-dimensional image dataset based on the identified target region; and actuating the medical imaging device based on the imaging parameter for the generation of the second three-dimensional image dataset.

19 Claims, 3 Drawing Sheets

(51) Int. Cl.
  *A61B 6/03*   (2006.01)
  *A61G 3/00*   (2006.01)
  *G06T 7/00*   (2017.01)
  *G06T 11/00*  (2006.01)
  *G06V 10/10*  (2022.01)

(52) U.S. Cl.
  CPC ............ *A61B 6/5217* (2013.01); *A61B 6/545* (2013.01); *A61G 3/001* (2013.01); *G06T 7/0012* (2013.01); *G06T 11/003* (2013.01); *G06V 10/10* (2022.01); *A61G 2210/50* (2013.01); *G06T 2200/04* (2013.01); *G06T 2207/10081* (2013.01); *G06T 2207/20081* (2013.01); *G06T 2207/30016* (2013.01); *G06V 2201/031* (2022.01)

(56) References Cited

U.S. PATENT DOCUMENTS

| | | |
|---|---|---|
| 2015/0289779 A1 | 10/2015 | Fischl et al. |
| 2017/0323447 A1 | 11/2017 | Tsukagoshi et al. |
| 2018/0025255 A1 | 1/2018 | Poole et al. |
| 2018/0365824 A1* | 12/2018 | Yuh ........................ G06V 10/82 |
| 2019/0117179 A1 | 4/2019 | Goyal |
| 2019/0200274 A1 | 6/2019 | Lautenschlaeger |
| 2019/0357862 A1* | 11/2019 | Bailey .................... A61B 6/04 |

\* cited by examiner

METHOD AND APPARATUS FOR ACTUATING A MEDICAL IMAGING DEVICE

PRIORITY STATEMENT

The present application hereby claims priority under 35 U.S.C. § 119 to European patent application number EP 19200340.8 filed Sep. 30 2019, the entire contents of which are hereby incorporated herein by reference.

FIELD

Embodiments of the invention generally relate to a method and an apparatus for actuating a medical imaging device via a control unit for generating a second three-dimensional image dataset which includes a target region in a region of interest of a patient with a functional impairment. Embodiments of the invention further generally relate to a vehicle including an apparatus for actuating a medical imaging device and a computer program product.

BACKGROUND

To treat a trauma patient or a stroke patient, a diagnosis is typically made by a physician and with the aid of medical image datasets. For a full analysis of a patient's medical situation, three-dimensional volume image data is frequently provided via a computed tomography device (CT device). This means that the imaging process is based on a plurality of X-ray projection measurement data items recorded from different angular ranges and a subsequent mathematical inverse transformation in order to reconstruct the three-dimensional volume image data based on the projection measurement data (for example via a filtered back projection reconstruction algorithm). This three-dimensional volume image data can also be used as the basis for the generation of two-dimensional slice image datasets which in each case depict a sectional image through the mapped volume.

In the case of a severe trauma or stroke, time is an important factor. The earlier correct treatment is commenced, the better the prospects of a successful outcome of the treatment, i.e. of avoiding or at least reducing permanent damage. In the case of a stroke, it can, for example, be extremely important that a thrombus be removed as quickly as possible to ensure the oxygen supply to the brain. A detailed diagnosis, and therefore the provision of image datasets that are as informative as possible, is essential for correct treatment.

Herein, a typical setup of an imaging series, in particular in the case of a stroke patient or of a suspected stroke, frequently consists of a native CT image dataset of the patient's head without contrast medium enhancement in order to enable other conditions or a hemorrhage-induced stroke to be excluded. In the case of an ischemic infarction, it is further possible for a CT angiography image dataset to be provided in order to identify the blood vessel occluded by a blood clot, i.e. which is affected by a vascular occlusion. In addition, frequently a CT perfusion image dataset is generated in order to identify the ischemic core region and the regions of the brain affected by a reduced blood flow but which are still potentially salvable. This image data can then be accordingly used as the basis of a targeted treatment decision, for example as to whether observation only, intravenous thrombolysis and/or even mechanical thrombectomy is required.

Therefore, the provision of image datasets in the most time-efficient manner as possible, the best possible coverage of the affected region by the image dataset and smooth image dataset generation are particularly desirable in the case of a stroke patient. At the same time, it is always necessary to avoid unnecessary exposure to radiation.

Embodiments of the invention provides an improved method and an improved apparatus for actuating a medical imaging device for generating a three-dimensional image dataset.

Further advantageous and partially per se inventive embodiments and developments of the invention are set out in the claims and the following description.

The following describes the inventive embodiments of the method and the claimed apparatus. Features, advantages or alternative embodiments can also be transferred to the other claimed subject matter and vice versa. In other words, the substantive claims (which are, for example, directed at an apparatus) can also be developed with features described or claimed in connection with the method. Herein, the corresponding functional features of the method are embodied by corresponding substantive modules.

At least one embodiment of the invention relates to a method for actuating a medical imaging device, in particular a mobile imaging device, via a control unit for generating a second three-dimensional image dataset which includes a target region in a region of interest of a patient with a functional impairment. For this purpose, the method according to an embodiment of the invention comprises: providing a first three-dimensional image dataset including the region of interest of the patient via a data processing unit, identifying the target region in the first three-dimensional image dataset via the data processing unit, wherein a partial region of the region of interest with the functional impairment is determined, determining an imaging parameter for the generation of the second three-dimensional image dataset based on the identified target region via the data processing unit, actuating the medical imaging device based on the imaging parameter for the generation of the second three-dimensional image dataset via the control unit.

At least one embodiment of the invention also relates to an apparatus for actuating a medical imaging device, in particular a mobile medical imaging device, for generating a second 3D image dataset including at least one target region of a region of interest of a patient with a functional impairment. The apparatus according to at least one embodiment of the invention includes a data processing unit embodied to provide a first 3D image dataset, to identify the target region in the first 3D image dataset, wherein a partial region of the region of interest affected by the functional impairment is determined, and to determine an imaging parameter based on the identified target region for generating the second 3D image dataset via the medical imaging device. The apparatus according to at least one embodiment of the invention also includes a control unit embodied to actuate the medical imaging device based on the imaging parameter determined for generating the second 3D image dataset.

At least one embodiment of the invention furthermore relates a vehicle, in particular an ambulance including a medical imaging device and an apparatus according to at least one embodiment of the invention.

Further, at least one embodiment of the invention is directed to a computer program product, which includes a computer program and can be loaded directly into a memory of a data processing unit, and program segments, for example libraries and auxiliary functions for executing a method for actuating a medical imaging device when the computer program product is executed.

At least one embodiment of the present invention is directed to a method for actuating a medical imaging device via a control unit for generating a second three-dimensional image dataset including a target region in a region of interest of a patient with a functional impairment, the method comprising:

providing a first three-dimensional image dataset including the region of interest of the patient, via a data processing unit;

identifying the target region based on the first three-dimensional image dataset, via the data processing unit, wherein a partial region of the region of interest with the functional impairment is determined;

determining an imaging parameter for generating the second three-dimensional image dataset based on the target region identified, via the data processing unit; and actuating the medical imaging device based on the imaging parameter determined for the generation of the second three-dimensional image dataset, via the control unit.

At least one embodiment of the present invention is directed to an apparatus for actuating a medical imaging device for generating a second three-dimensional image dataset including at least one target region in a region of interest of a patient with a functional impairment, the apparatus comprising:

a data processing unit embodied
  to provide a first three-dimensional image dataset including the region of interest of the patient,
  to identify the target region, based on the first three-dimensional image dataset, wherein a partial region of the region of interest with a functional impairment is determined and
  to determine an imaging parameter based on the target region identified, for generating the second three-dimensional image dataset; and
a control unit embodied to actuate the medical imaging device based on the imaging parameter determined for generating the second three-dimensional image dataset.

At least one embodiment of the present invention is directed to a non-transitory computer program product storing a computer program, directly loadable into a memory of a data processing unit, including program segments for executing the method for actuating a medical imaging device of an embodiment when the computer program is executed by the data processing unit.

At least one embodiment of the present invention is directed to a non-transitory computer readable medium storing a computer program, readable and executable by a data processing unit, including program segments for executing the method for actuating a medical imaging device of an embodiment when the computer program is executed by the data processing unit.

BRIEF DESCRIPTION OF THE DRAWINGS

The following describes the invention with reference to example embodiments and with reference to the accompanying figures. The depiction in the figures is schematic, greatly simplified and not necessarily true to scale. The drawings show.

DETAILED DESCRIPTION OF THE EXAMPLE EMBODIMENTS

Figure 1:
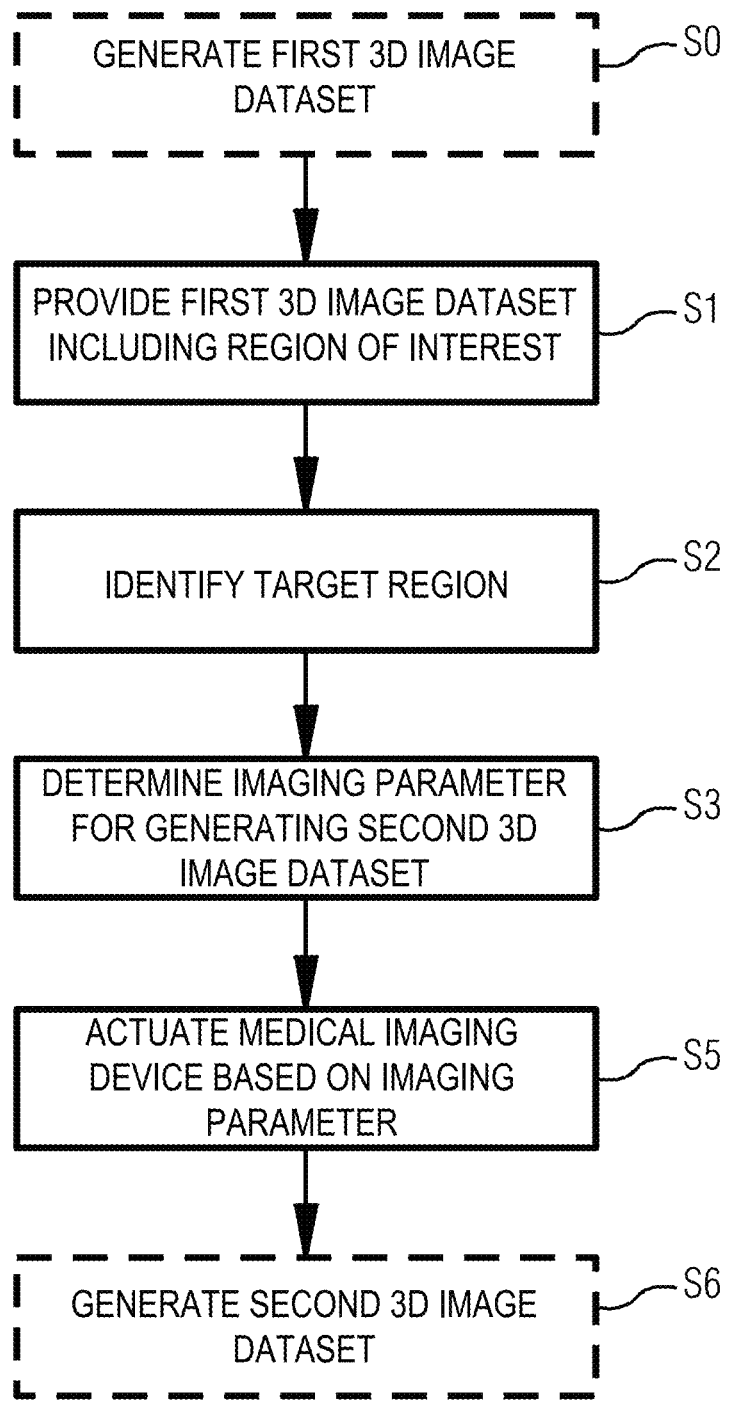
FIG. 1 a method according to an embodiment of the invention for actuating a medical imaging device, FIG. 2 a schematic depiction of a longitudinal section through a 3D image dataset, FIG. 3 a further, schematic depiction of a cross section through a 3D image dataset, FIG. 4 a vehicle including a medical imaging device and an apparatus according to an embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central At least one processor (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central At least one processor (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer at least one processors into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for actuating a medical imaging device, in particular a mobile imaging device, via a control unit for generating a second three-dimensional image dataset which includes a target region in a region of interest of a patient with a functional impairment. For this purpose, the method according to an embodiment of the invention comprises:

providing a first three-dimensional image dataset including the region of interest of the patient via a data processing unit, identifying the target region in the first three-dimensional image dataset via the data processing unit, wherein a partial region of the region of interest with the functional impairment is determined, determining an imaging parameter for the generation of the second three-dimensional image dataset based on the identified target region via the data processing unit, and actuating the medical imaging device based on the imaging parameter for the generation of the second three-dimensional image dataset via the control unit.

In particular, the medical imaging device can be used to generate a three-dimensional image dataset (3D image dataset), for example a computed tomography image dataset (CT image dataset). Herein, the generation of a 3D image dataset can include image acquisition, i.e. the recording of the measurement data via a measurement data recording unit of the medical imaging device. The measurement data recording unit includes, for example, an X-ray source and an X-ray detector, which is positioned relative to the patient for the recording of measurement data. In addition, the generation can also include image reconstruction of the 3D image dataset on the basis of recorded measurement data.

A 3D image dataset permits a three-dimensional, in particular spatially three-dimensional, depiction of the region of interest of the patient. A 3D image dataset can also be depicted as a plurality of slice image datasets. A slice image dataset in each case includes a slice of the 3D image dataset at a position along a marked axis. A slice image dataset then in each case permits a two-dimensional, in particular spatially two-dimensional, depiction of the respective slice.

The 3D image dataset advantageously includes a plurality of voxels, in particular image points. Herein, each voxel can preferably in each case have a value, in particular an image value, for example a gray value and/or an RGB color value and/or an intensity value. Analogously, a slice image dataset can include a plurality of pixels, in particular image points. Herein, each pixel can preferably in each case have a value, in particular an image value, for example a gray value and/or an RGB color value and/or an intensity value.

The medical imaging device can, for example, include a CT device or a C-arm X-ray device. Also conceivable are other imaging devices embodied to generate a 3D image dataset.

The patient can be an animal patient and/or a human patient. Further, the region of interest of the patient can include an anatomical and/or spatial region of the patient which includes a predetermined tissue region and/or a spatial region required for a diagnosis. Herein, the region of interest can include a body region, for example the head, the thorax or an arm. The region of interest can optionally also include the entire patient's body.

The first 3D image dataset provided in particular includes the region of interest of the patient. The provision of the first 3D image dataset can, for example, include acquiring and/or reading out a computer-readable data memory and/or reception from a memory unit. The method according to the invention can further also include the generation of the first 3D image dataset via the medical imaging device, which can subsequently be provided for the further steps of the method.

In particular the first 3D image dataset can be or have been generated by the same medical imaging device as the second 3D image dataset. However, herein, the first 3D image dataset can be or have been generated via a different recording mode of the medical imaging device than the second 3D image dataset. For example, the first 3D image dataset is a native CT image dataset or a CT angiography image dataset and the second 3D image dataset a CT perfusion image dataset. Other recording modes or image datasets are also conceivable.

According to the method according to an embodiment of the invention, the second 3D image dataset includes a target region of the region of interest of a patient with a functional impairment. Herein, a functional impairment can mean that the normal, bodily function of a functional unit of the patient's body included by the region of interest is disrupted or restricted. A functional unit can, for example, be an organ, a bone, a blood vessel or the like. In the specific example of a stroke patient, the functional unit can, for example, be the patient's brain.

The target region included by the region of interest can then at least include the partial region of the region of interest with the functional impairment, i.e. in which the functional impairment can be localized based on the first 3D image dataset. This can mean that the target region can at least include the partial region of the region of interest with which the functional impairment can be associated, i.e. linked, in the first 3D image dataset. This can mean that the target region can include a functional unit affected by the functional impairment, a subunit of the affected functional unit to which the functional impairments can be restricted, or also a specific point of origin of the functional impairment within the functional unit.

The step of identifying the target region can then include a localization of the partial region of the region of interest in the first 3D image dataset which can be linked with the functional impairment based on the first 3D image dataset. This means that it is possible to identify image regions corresponding to the partial region in the first 3D image dataset. It can also include the localization of a site, i.e. a site of occurrence or a site of origin, of the functional impairment in the region of interest based on the first 3D image dataset. This means that the identifying step can, for example, include the localization or determination of a functional unit affected by the functional impairment, a subunit of the affected functional unit to which the occurrence of the functional impairments can be restricted, or also a specific site of origin of the functional impairment within the functional unit based on the first 3D image dataset.

The identified target region can be identified as a three-dimensional volume in the first 3D image dataset. It can also be identified as a two-dimensional area in one or in each of a plurality of slice image datasets of the first 3D image dataset. The identified target region can also be determined by individual or a plurality of pixel or voxel coordinates in the first 3D image dataset or one of its slice image datasets. For example, the target region identified is highlighted in a depiction of the first 3D image dataset for a user. For example, a marking can be depicted in the form of a three-dimensional or two-dimensional box in the image dataset superimposed on the image data, which marks the identified target region in the first 3D image dataset. This can optionally enable a user to check the identified target region.

An example of functional impairment is an insufficient supply of oxygen and glucose to a region of the brain following a vascular occlusion of a cerebral artery, i.e. a perfusion deficit in the context of an ischemic infarction. The target region can then include the brain as a functional unit. This means that, during the identification, the image regions associated with the brain of a patient can be determined in the first 3D image dataset. The target region can also include the part of the brain as a subunit of the affected functional unit, which can be determined as affected by the perfusion deficit or linked thereto in the first 3D image dataset. This means that, during the identification, it is possible to determine the image regions of the first 3D image dataset that can be linked with the perfusion deficit. The target region can include the actual ischemic core region depicting the center of the perfusion deficit. Here, the maximum blood flow is only 20% of the normal perfusion amount, which leads to an irreversible loss of function in an extremely short time. On the other hand, in the penumbra surrounding the core region, also called the core shadow, it is possible for the tissue to recover as a result of residual blood flow in the brain tissue provided that the patient is given the appropriate treatment promptly. This means that, during the identification, it is possible to identify the image regions that can be linked to the ischemic core region in the first 3D image dataset.

Another example of a functional impairment is, for example, a fracture of a skeletal bone. The target region then, for example, includes at least the region of the site of the fracture. However, the target region can also, for example, include the entire, affected bone or the section of the patient's body including the bone. A further example of a functional impairment is, for example, a vascular occlusion of a blood vessel away from the brain, for example in the heart. The target region then, for example, includes at least the site or the vascular segment at which the vascular occlusion is present. In addition, there may still be other applications of the method according to at least one embodiment of the invention.

In addition, it is furthermore conceivable for the identification also to include the determination of an expansion of the functional impairment or a volume of a region affected by the functional impairment, for example a maximum expansion along at least one spatial dimension of the 3D image dataset.

The identification can take place in the first 3D image dataset and/or based on slice image datasets of the 3D image datasets. Herein, the identification can in particular be based on an analysis or further processing of the image values or the structures mapped thereby in the first 3D image dataset or its slice image datasets.

The imaging parameter determined based on the target region can include an imaging parameter relating to the image acquisition and/or the image reconstruction. The imaging parameter determined can in particular be targeted to match the generation of the second 3D image dataset to the identified target region, i.e. in particular the partial region of the region of interest with the functional impairment defined by the target region identified via the first 3D image dataset. This can result in an optimal depiction of the region with the functional restriction via the second 3D image dataset.

It is also possible for more than one imaging parameter to be determined. For example, a recording region, also called a scan region, can be specified based on the target region. The recording region can correspond to the part of the patient or the region of interest for which measurement data is to be recorded via the medical imaging device for the generation of the second 3D image dataset. The imaging parameter can include a positioning parameter of the medical imaging device, in particular the measurement data recording unit thereof, relative to the patient or relative to the region of interest. The imaging parameter can also include a reconstruction volume for the reconstruction of the 3D image dataset or also another type of reconstruction parameter. In addition, other imaging parameters are also conceivable.

Herein, the steps of identifying and/or determining can be carried out fully automatically and without further user intervention via the data processing unit. However, it is also possible for interaction with a user to be provided, for example a confirmation or possibility of correction for the target region or the imaging parameter or the like by a user. For this, in particular an input unit can be provided which is embodied to convert user inputs in the form of touch, gestures, speech or the like into instructions that can be interpreted for the data processing.

Based on the imaging parameter determined, according to at least one embodiment of the invention, the medical imaging device is actuated via the control unit. For this, the imaging parameter can, for example, be output via an interface to the control unit of the medical imaging device. Before or also after being output to the control unit, the imaging parameter can be translated into a control instruction for the medical imaging device, which can be interpreted by the control unit for the actuation of the imaging process, i.e. the generation of the second 3D image dataset. Similarly to the imaging parameter determined, actuation via the control unit can include actuation of the image acquisition and/or actuation of the image reconstruction.

Herein, the actuation step can be carried out fully automatically and without further user intervention via the control unit based on the imaging parameter determined. However, interaction with a user can also be provided, for example a confirmation, a starting or stopping, a possibility of correction or the like by a user.

The second 3D image dataset can in particular depict a partial section of the first 3D image dataset which includes at least the target region. There can also be cases in which the second 3D image dataset depicts the same image section as the first 3D image dataset, provided, for example, that such a recording region is determined as an imaging parameter via the method according to at least one embodiment of the invention.

The second 3D image dataset is preferably generated in chronological proximity to the first 3D image dataset. Herein, particularly preferably, a movement of the patient, in particular the region of interest, between the first and second image dataset is avoided as far as possible.

The inventors have recognized that in many imaging procedure cases at least two successive image datasets are recorded in in chronological proximity so that it is possible to use a pre-existing first image dataset to optimize and, if possible, also automate the imaging process for generating the subsequent second image dataset. In particular, this is the case if different image modalities, for example a native CT image dataset and a CT angiography image dataset or a CT perfusion image dataset, are to be performed in a short time sequence, and preferably without moving the patient, and combined for a comprehensive diagnosis. Advantageously, the method enables a particularly time-efficient workflow. In particular, it is possible to reduce time-consuming and error-prone manual steps and adjustments for the generation of the second 3D image dataset. Likewise, the method can advantageously help to minimize the dose in that an imaging parameter is selected, for example an optimized recording region, thus enabling unnecessary radiation exposure to be avoided and repetitions of recordings to be reduced.

For particularly time-critical applications, for example in the case of a trauma patient or stroke patient, current developments also enable a more flexible use of CT devices, for example in ambulances (so-called mobile stroke units) or even in helicopters, that enable a patient to be examined in an even shorter time. However, these are usually subject to restrictions, for example due to the limited space available. For example, only a limited recording region may be available. In these cases, as well as a particularly smooth process, it is also necessary for there to be an optimal selection of the relevant body region for the generation of an informative image dataset. Advantageously, the method according to at least one embodiment of the invention enables it to be ensured that a relevant partial region can be selected optimally and mapped via the second 3D image dataset.

In one variant of the method according to at least one embodiment of the invention, the region of interest includes at least one part of the patient's head and the target region at least one part of the patient's brain.

The target region can include the whole brain or only a part of the brain. The patient can be a trauma patient with potential injuries or bleeding in the brain. In particular, the patient can be a stroke patient with an ischemic infarction.

On the occurrence of functional impairments, for example caused by an ischemic infarction, relating to the brain, as a rule a particularly prompt and comprehensive diagnosis is essential for optimal treatment of the patient so that here the method according to at least one embodiment of the invention can be used particularly advantageously. In addition, in such cases frequently after a first, generally native, image dataset without the addition of contrast media, the combination with at least one second recording mode, for example a CT angiography image dataset or a CT perfusion image dataset, is provided for the diagnosis so that advantageously, as a rule, a first three-dimensional image dataset is already available and can be used for the actuation of the medical imaging device for generating the second 3D image dataset. A time-efficient exact determination of a target region and an actuation matched thereto can in particular be essential for a successful generation of the two-dimensional image dataset if the time-critical application is accompanied by restrictions of the medical imaging device.

Furthermore, it is provided in one embodiment of the method that the patient is a stroke patient and, in the step of identifying the target region as a partial region, a part of the brain of a patient affected by an ischemic infarction is determined.

A stroke, i.e. in particular an ischemic infarction, represents a particularly time-critical application, wherein a diagnosis that is as fast and comprehensive as possible is essential with respect to the extent of subsequent impairments and the survival of the patient, so that the method according to at least one embodiment of the invention can be used particularly advantageously here.

Herein, the determination of the partial region can in particular be based on an analysis or further processing of the image values that occur or structures generated thereby in the first 3D image dataset or its slice image datasets.

For example, a patient's brain can be divided into different brain areas based on the first 3D image dataset. The brain areas can be, for example, but do not necessarily have to be, linked with specific bodily functions. The brain can, for example, be divided into the brain areas based on an anatomical atlas. For example, the brain areas can in each case be evaluated with respect to the probability of their being affected by the ischemic infarction. A respective brain area can be partially or wholly affected by the ischemic infarction. Accordingly, the target region can then include at least one brain area evaluated as affected. The target region can also affect more than one brain area evaluated as affected. Herein, the evaluation can be based on the analysis or further processing of the image values.

The partial region affected by an ischemic infarction can also be determined independently of a previous division into different brain areas in that the image values that occur or structures generated thereby in the first 3D image dataset or its slice image datasets are analyzed or further processed.

An affected partial region can, for example, in the first 3D image dataset or in a respective slice image dataset of the first 3D image dataset, have local or global image values, spatially coherent groups of image values, an average image value or the like, which, for example, differ or differs from an expected value. Herein, an expected image value can be based on non-affected brain areas of the patient, for example by comparing the right and left hemispheres of the brain or also on empirical values from previously recorded image datasets of the actual patient or a plurality of patients.

Herein, the partial region determined can represent a three-dimensional volume in the first 3D image dataset or, when viewing the first 3D image dataset slice-by-slice, a two-dimensional area in a slice of the first 3D image dataset.

In a particularly advantageous embodiment of the method, an ischemic core region is determined in the first 3D image dataset in the identifying step.

The ischemic core region includes the region with irreversible damage to the brain caused by the perfusion deficit. As a rule, the ischemic core region is located in the center of a brain area affected by a perfusion deficit and is surrounded by the penumbra, in which there is residual bleeding. Hence, the ischemic core region can particularly advantageously be used for localization and determination of the relevant region. The determination of the ischemic core region can also optionally enable conclusions to be drawn regarding the origin and extent of and the damage caused by the ischemic infarction.

One variant of the method according to at least one embodiment of the invention provides that the target region is identified automatically in the first 3D image dataset based on a segmentation algorithm or a threshold method.

The segmentation algorithm can, for example, be based on pixel-based, voxel-based, edge-based, area-based and/or region-based segmentation. The segmentation can also be based on a model-based, atlas-based method in conjunction with assumptions about the object to be segmented. Herein, the segmentation can proceed in a slice-by-slice manner, i.e. on the basis of the two-dimensional slice images, or it is also possible to use a three-dimensional segmentation method. Herein the segmentation step can also be implemented in a semi-automatic manner. For example, starting points or germ cells or rough contour information can be set manually for the segmentation.

A segmentation algorithm can advantageously be used to identify coherent structures. For example, the brain, brain areas or partial regions of the brain affected by ischemic infarction can be segmented.

A threshold method can include a comparison of image values of the first 3D image dataset, for example given in HU ("Hounsfield Units"), with a threshold value. This can, for example, be used to differentiate whether or not the pixel or voxel with the image value should be assigned to the target region. Herein, the threshold value can correspond to an above-described expected value. A segmentation algorithm can be based on a threshold method or precede this method, wherein image regions with an image value below or above the specified threshold value are assigned to a region to be segmented or the image dataset for a segmentation is prepared via a threshold method.

Herein, it can be provided that the identifying step includes the application of a trained function.

A trained function can be used to determine the target region automatically and in a time-efficient manner. A trained function can, for example, be used for a localization, a segmentation and/or an evaluation of brain areas. A trained function can optionally even be used to derive the imaging parameter based on the target region.

Herein, the trained function can advantageously be trained using a machine learning method. In particular, the trained function can be a neural network, in particular a convolutional neural network (CNN) or a network including a convolutional layer.

A trained function maps input data onto output data. Here, the output data can in particular furthermore depend upon one or more parameters of the trained function. The one or more parameters of the trained function can be determined and/or adjusted by training. The determination and/or the adjustment of the one or more parameters of the trained function can in particular be based on a pair consisting of training input data and associated training output data, wherein the trained function is applied in order to generate output data onto the training input data. In particular, the evaluation can be based on a comparison of the generated output data and the training output data. A trainable function, i.e. a function with one or more parameters that have not yet been adjusted, is generally referred to as a trained function.

Other terms for trained function are trained mapping rule, mapping rule with trained parameters, function with trained parameters, algorithm based on artificial intelligence, machine learning algorithm. An example of a trained function is an artificial neural network, wherein the edge weights of the artificial neural network correspond to the parameters of the trained function. Instead of the term "neural network", it is also possible to use the term "neural net". In particular, a trained function can also be a deep artificial neural network (or deep neural network). A further example for a trained function is a "support vector machine", furthermore in particular it is also possible to use other machine learning algorithms as a trained function. The trained function can, for example, be trained via back propagation. First, output data can be determined by applying the trained function to training input data. After this, it is possible to ascertain a difference between the generated output data and the training output data by applying an error function to the generated output data and the training output data. Further, at least one parameter, in particular a weighting, of the trained function, in particular the neural network, can be adjusted iteratively based on a gradient of the error function with respect to the at least one parameter of the trained function. This can advantageously enable the difference between the training mapping data and the training output data during the training of the trained function to be minimized.

The training input data can, for example, include a plurality of 3D training image datasets with a functional impairment. The training output data can, for example, include training image datasets with localized partial regions or linked target regions, evaluations of brain areas or imaging parameters.

The application of an artificial intelligence system, i.e. a trained function, enables all influencing variables relevant for the identification to be taken into account, including those for which a user is unable to estimate a connection with the identification. In particular, after the training phase, a trained function can enable automated identification in a particularly reliable and time-efficient manner.

In one embodiment of the method, the imaging parameter is an image acquisition parameter for recording measurement data for generating the second 3D image dataset and/or an image reconstruction parameter for the image reconstruction of the second 3D image dataset.

Advantageously, automation or at least partial automation of the imaging process, i.e. the generation, is enabled. Advantageously, it is possible to optimize the imaging process by avoiding error-prone manual steps and by improved time efficiency.

Herein, an image acquisition parameter can substantially include any parameter relating to the recording of measurement data. For example, the imaging parameter can relate to a recording region. The recording region can specify which region of the region of interest is to be scanned via the medical imaging device for the generation of the second 3D image dataset. It can also include other parameters for the recording of measurement data. For example, setting parameters for the measurement data recording unit, for example for setting the X-ray source or the X-ray detector. The imaging parameter can also relate to a positioning parameter of the measurement data recording unit relative to the patient or a movement parameter of the measurement data recording unit relative to the patient, for example a speed of the movement.

Particularly preferably, the imaging parameter determined includes at least one recording region.

Advantageously, an optimized recording region, which in particular can also incorporate the circumstances of the medical imaging device, can be provided. Advantageously, a dose-optimized recording region can be provided.

Furthermore, the method according to at least one embodiment of the invention can include that the imaging parameter determined includes a recording region for the recording of measurement data via the medical imaging device for generating the second 3D image dataset and the actuation includes positioning a measurement data recording unit of the medical imaging device relative to the patient based on the recording region determined for the recording of the measurement data.

Advantageously, a positioning parameter for the measurement data recording unit for recording measurement data of the recording region can be derived from the recording region determined. The positioning parameters can furthermore be diverted into control commands for positioning the measurement data recording unit via the control unit on the basis of which the medical imaging device is actuated. Advantageously, particularly time-efficient and optimally matched generation of the second 3D image dataset is enabled. Advantageously, the positioning can be automated or at least partially automated and error-prone and possibly laborious manual positioning dispensed with. Overall, this can advantageously enable an optimized, and in particular automated, imaging process and hence a time-efficient and dose-efficient process. Herein, this can in particular include an optimal selection of the region relevant for a more in-depth diagnosis.

Herein, the positioning of a measurement data recording unit of the medical imaging device relative to the patient can include the positioning of the actual measurement data recording unit. Herein, the positioning of a measurement data recording unit of the medical imaging device relative to the patient can also include the positioning of the patient via a mobile mounting apparatus, that can be actuated via the control unit, on which the patient is mounted for the generation of the second 3D image dataset and which is included by the medical imaging device.

The imaging parameter determined can include a parameter relating to the image reconstruction. For example, it is possible to determine a reconstruction volume, a parameter of a reconstruction method, a parameter relating to artifact correction included by the reconstruction or also another type of parameter. Advantageously, a reconstruction matched to the target region can be provided automatically.

Particularly preferably, the method according to at least one embodiment of the invention includes the fact that the imaging parameter determined includes a reconstruction volume.

Advantageously, the image reconstruction of the second 3D image dataset can be carried out automatically or at least semi-automatically and enable a time-efficient and optimized imaging process. Advantageously, it is possible to ensure a reconstruction volume that is optionally matched to the recording region and/or the positioning of the measurement data recording unit.

An in particular automatic matching of the image acquisition parameters and/or image reconstruction parameters based on the target region identified in the first 3D image dataset can advantageously enable an optimized imaging process and hence a time- and dose-efficient process.

In one embodiment of the method, the first three-dimensional image dataset is a native image dataset, in particular a native CT image dataset, or an angiography image dataset, in particular a CT angiography image dataset, and the second image dataset is a perfusion image dataset, in particular a CT perfusion image dataset.

A CT perfusion image dataset is frequently used in very time-critical applications, in particular with a stroke patient. Herein, particularly frequently, a previous image dataset, i.e. a native CT image dataset or a CT angiography image dataset, is generated in advance of a CT perfusion image dataset. In particular for example in the context of a mobile medical imaging device, a CT perfusion image dataset is frequently associated with restrictions with respect to the scannable recording region. Advantageously, the method according to at least one embodiment of the invention enables an optimized imaging process which makes optimal use of the possibly restricted recording region or at least enables a generation of the perfusion image dataset that is as time- and dose-efficient as possible.

Furthermore, the method according to at least one embodiment of the invention can include that, in the case of a plurality of first image datasets, the first image dataset with the shortest time interval to the time of the provision is provided for the identification.

If, for example, both a native CT image dataset without the addition of contrast medium and a CT angiography image dataset are available, it is in particular possible for the most recently recorded image dataset to be used and to be provided for the method. Advantageously, the smallest possible change to the patient position, i.e. movement of the region of interest, between the first and the second image dataset is to be expected.

At least one embodiment of the invention also relates to an apparatus for actuating a medical imaging device, in particular a mobile medical imaging device, for generating a second 3D image dataset including at least one target region of a region of interest of a patient with a functional impairment. The apparatus according to at least one embodiment of the invention includes a data processing unit embodied to provide a first 3D image dataset, to identify the target region in the first 3D image dataset, wherein a partial region of the region of interest affected by the functional impairment is determined, and to determine an imaging parameter based on the identified target region for generating the second 3D image dataset via the medical imaging device. The apparatus according to at least one embodiment of the invention also includes a control unit embodied to actuate the medical imaging device based on the imaging parameter determined for generating the second 3D image dataset.

An apparatus according to at least one embodiment of the invention for actuating a medical imaging device can in particular be embodied to execute the above-described method according to at least one embodiment of the invention and the aspects thereof. The apparatus for actuating a medical imaging device can be embodied to execute the method and the aspects thereof in that the data processing unit and the control unit are embodied to execute the corresponding method steps.

Herein, the variants, features and advantages of the method and its embodiments can likewise also be transferred directly to the apparatus.

In a preferred variant of the apparatus, the medical imaging device is in particular a CT device. Herein, the CT device can in particular be embodied, in addition to native CT image datasets, to generate angiography CT image datasets and perfusion CT image datasets.

At least one embodiment of the invention furthermore relates a vehicle, in particular an ambulance including a medical imaging device and an apparatus according to at least one embodiment of the invention.

Herein, the variants, features and advantages of the method and its embodiments can likewise be transferred directly to the vehicle.

Further, at least one embodiment of the invention is directed to a computer program product, which includes a computer program and can be loaded directly into a memory of a data processing unit, and program segments, for example libraries and auxiliary functions for executing a method for actuating a medical imaging device when the computer program product is executed.

Herein, the computer program product can include software with a source code that still has to be compiled and linked or only has to be interpreted or an executable software code that only needs to be loaded into the data processing unit for execution. The computer program product enables the method for actuating a medical imaging device to be executed quickly and robustly, and to be identically repeated. The computer program product is configured such that it can execute the method steps according to at least one embodiment of the invention via the data processing unit. Herein, the data processing unit must in each case fulfil the requisite conditions such as, for example, an appropriate random-access memory, an appropriate graphics card or an appropriate logic unit so that the respective method steps can be executed efficiently.

The computer program product is for example stored on a computer-readable medium or held on a network or server from where it can be loaded into the processor of a data processing unit, which can be directly connected to the data processing unit or embodied as part of the data processing unit.

Furthermore, program segments of the computer program product can be stored on an electronically readable data carrier. The program segments of the electronically readable data carrier can be embodied such that they carry out a method according to at least one embodiment of the invention when the data carrier is used in a processing unit. Examples of electronically readable data carriers are a DVD, a magnetic tape or a USB stick, on which electronically readable program means, in particular software, are stored. When these program means are read by the data carrier and stored in a processing unit, all the embodiments according to at least one embodiment of the invention of the above-described method can be carried out. Thus, the invention can also be based on the computer-readable medium and/or the electronically readable data carrier.

An extensively software-based implementation has the advantage that it is possible to retrofit apparatuses used to date for actuating a medical imaging device in a simple way via a software update in order to work in the manner according to at least one embodiment of the invention. In addition to the computer program, such a computer program product can optionally include additional parts, such as, for example, documentation and/or additional components and hardware components, such as, for example, hardware keys (dongles etc.) for using the software.

FIG. 1 depicts an example schematic process of a method for actuating a medical imaging device 101, in particular a mobile medical imaging device, via a control unit 113 for generating a second three-dimensional image dataset which includes a target region 11 in a region of interest 3 of a patient 103 with a functional impairment.

In a providing step S1, a first three-dimensional image dataset including the region of interest 3 of the patient 103 is provided via a data processing unit 115.

In a next identifying step S2, the target region 11 based on the first three-dimensional image dataset is identified via the data processing unit 115, wherein a partial region of the region of interest 3 with the functional impairment is determined.

Herein, in one variant of the method, the region of interest 3 includes at least one part of the head of the patient 103 and the target region 11 at least one part of the brain 13 of the patient 103.

In particular, the patient 103 can be a stroke patient, wherein in the step S2 of identifying the target region 11 as a partial region, a part 8,9 of the brain 13 of the patient 103 affected by an ischemic infarction affected is determined.

Herein, in particular the actual ischemic core region 9 can be determined.

Herein, the target region 11 can be identified based on a segmentation algorithm, a threshold method and/or with the aid of an anatomical atlas and in particular automatically based on the first three-dimensional image dataset.

In particular, the identifying step S2 can include the application of a trained function.

In a further determining step S3, an imaging parameter 4 for generating the second three-dimensional image dataset is determined based on the identified target region 11 via the data processing unit 115.

Herein, the imaging parameter 4 can be an image acquisition parameter 6,7 for recording measurement data for generating the second three-dimensional image dataset and/or an image reconstruction parameter 5 for image reconstruction of the second three-dimensional image dataset.

In particular the imaging parameter 4 can be a recording region 6,7 and/or a reconstruction volume 5.

In a further actuating step S5, the medical imaging device 101 is actuated based on the imaging parameter 4 determined for the generation of the second three-dimensional image dataset via the control unit 113.

For example, the imaging parameter 4 determined is a recording region 6,7 for the recording of measurement data via the medical imaging device 101 for generating the second three-dimensional image dataset and the actuation a positioning of a measurement data recording unit 102,104 of the medical imaging device 101 relative to the patient 103.

The method can further include a step of the first generation S0 of the first 3D image dataset.

The method can further include a step of the second generation S6 of the second 3D image dataset in the context of the actuation of the medical imaging device.

In particular, the first three-dimensional image dataset can be a native image dataset or an angiography image dataset, and the second three-dimensional image dataset can be a perfusion image dataset.

In particular, in the case of a plurality of first three-dimensional image datasets, advantageously the first three-dimensional image dataset with the shortest time interval to the time of the provision can be provided.

Figure 2:
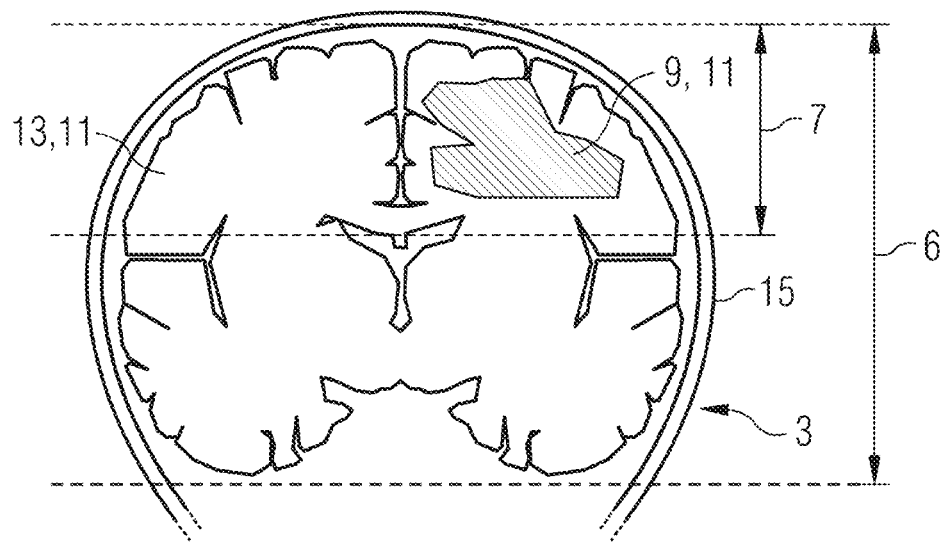
Figure 3:
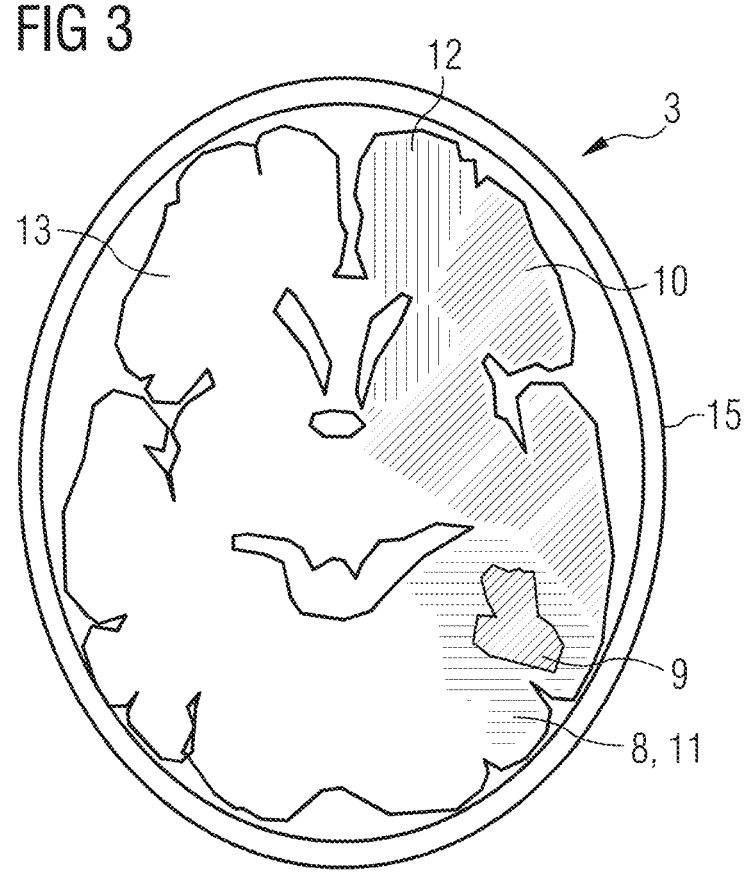

To illustrate a possible target region 11, FIG. 2 and FIG. 3 in each case show a schematic depiction of a longitudinal section or of a cross section through a first 3D image dataset. Such a section can substantially correspond to a slice image dataset of the first 3D image dataset.

Only section image datasets of a first 3D image dataset are depicted here. However, the identification of the target region 11 and determination of the imaging parameter 6,7 can be easily transferred to a spatially three-dimensional depiction of the first 3D image dataset.

Herein, the region of interest 3 included by the first 3D image datasets depicted by way of example in FIGS. 2 and 3 is in particular at least one part of the head 3 of a stroke patient 103 with a functional impairment due to an ischemic infarction. In each case, these indicate the cranial bone 15 and the brain 13 of the patient 103 in the sectional image of the first 3D image dataset depicted in each case. For the example image datasets depicted in FIGS. 2 and 3, it is in each case assumed that there is a perfusion deficit in the region 9 due to the ischemic infarction. In particular, in the examples shown, the region 9 substantially corresponds to the ischemic core region in each case.

In the identifying step, according to the method according to an embodiment of the invention, the target region 11 is identified based on the first 3D image dataset via the data processing unit 115, wherein a partial region of the region of interest 3 with the functional impairment is determined. This can substantially include the identification of the image regions which can be linked with the functional impairment in the first 3D image dataset.

FIG. 2 depicts by way of example that the target region 11 can include the entire brain 13 of the patient 103 as a partial region of the head 3 with the functional impairment. For example, herein, the brain 13 of the patient can be identified or localized in the identifying step based on the image values in the first 3D image dataset via a threshold method, a segmentation method or via a trained function. On the basis of this, for example, it is possible to determine an optimized recording region 6 and/or an optimized reconstruction volume 6 including the region of the brain 13 of the patient 103.

Furthermore, a determined recording region 6 can, for example, be used as the basis for determining a positioning parameter based on the recording region 6 for the medical imaging device 101 for generating the second 3D image dataset, which is subsequently applied in the actuating step via the control unit 115 for generating the second 3D image dataset.

As alternatively depicted in FIG. 2, it is also possible for only a part of the brain 13 affected by the functional impairment, here the ischemic infarction, to be determined as a partial region and hence included by the identified target region 11. The ischemic core region 9 can optionally be identified based on the first 3D image dataset and determined as a target region 11. For example, the image values in the ischemic core region differ from the image values away from the ischemic core region. For example, the ischemic core region 9 can be identified automatically based on a segmentation algorithm or a threshold method in the first 3D image dataset.

For this, it is for example also possible to use a machine learning method, i.e. the application of a trained function, to be provided. Based on the ischemic core region, it is in turn possible for an imaging parameter matched to the target region to be determined in the form of a recording region 7 or reconstruction volume 7. In this case, the recording region 7 can be reduced to a part of the brain 13 of the patient 103, thus advantageously enabling dose savings and better account to be taken of any restrictions of the medical imaging device 101 with respect to a recording region.

Alternatively, as depicted in FIG. 3 by way of example and only schematically, in the identifying step, the brain 13 of a patient 103 can first also be divided in a plurality of brain areas 8, 10, 12 based on the first 3D image dataset. The brain areas 8, 10, 12 can, for example, but do not necessarily have to, be linked with specific bodily functions. For example, then a brain area 8 can be evaluated as affected by the functional impairment and identified as a target region 11. The brain area 8 can be identified as a target region 11 in that the image values that occur or structures that occur in the first 3D image dataset or are in each case analyzed or further processed separately in the brain areas 8, 10, 12. Due to the occurrence of the perfusion deficit in this area, the brain area 8 can, for example, have an average image value which differs from an expected value. Herein, an expected image value can be based on non-affected brain areas of the patient 103, for example by a comparison of the right and left hemispheres of the brain 13 or also on empirical values from previously recorded image datasets of the actual patient 103 or a plurality of patients.

A brain area 8,10,12 can also be determined in another way as a partial region affected by the functional impairment, for example if local or global image values, spatially coherent groups of image values, or other structures, for example fluctuations between the image values that occur, occur, which can be linked with a functional impairment. For example, the application of a trained function can ensure that an affected brain area is identified in a time-efficient and reliable manner.

In this case, it can also be advantageous to determine a recording region and/or a reconstruction volume, not depicted in further detail here, which can be restricted to a part of the brain including the area 8, thus advantageously enabling dose savings and better account to be taken of any restrictions of the medical imaging device with respect to a recording region.

Figure 4:
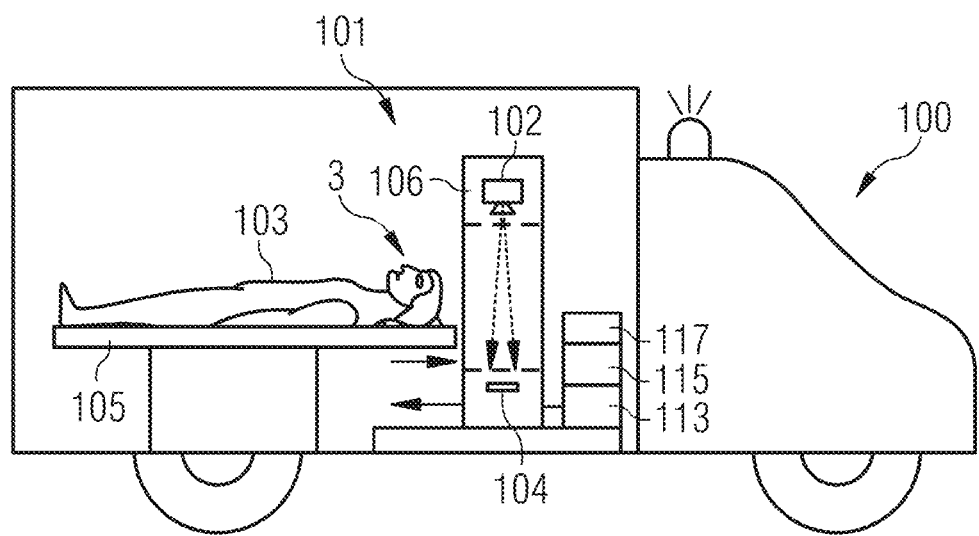

FIG. 4 shows a vehicle, in particular an ambulance, including a medical imaging device 101 and an apparatus for actuating the medical imaging device 101 for generating a second three-dimensional image dataset including at least one target region 11 in a region of interest of a patient 103, in particular a stroke patient, with a functional impairment.

In this example, the medical imaging device 101 is a computed tomography device with a measurement data recording unit 102,104 including an X-ray detector 104 and, opposite thereto, an X-ray source 102, which are arranged in a gantry 106 that enables rotation of the measurement data recording unit 102,104 about a common axis and hence the recording of measurement data, i.e. in particular X-ray projection measurement data, of a patient 103 from different angular ranges. This measurement data can then be used as the basis for reconstructing a first or second three-dimensional image dataset, for example via a filtered back projection reconstruction algorithm or corresponding slice image datasets.

Herein, the patient 103 is mounted on a patient mounting apparatus 105 of the medical imaging device 101. To record measurement data, the measurement data recording unit 102,104 is positioned relative to the patient so that a determined recording region 6,7 can be scanned via the measurement data recording unit 102,104. A positioning, indicated by way of example by the arrows, can be enabled by moving or positioning the patient mounting apparatus 105 and/or also by moving or positioning the measurement data recording unit 102,104, i.e. substantially the gantry 106.

The apparatus for actuating the medical imaging device 101 in particular comprises a data processing unit 115 embodied to provide a first three-dimensional image dataset including the region of interest 3 of the patient 103, to identify the target region 11 based on the first three-dimensional image dataset, wherein a partial region of the region of interest with the functional impairment is determined, and to determine an imaging parameter 4 based on the identified target region 11 for generating the second three-dimensional image dataset.

The apparatus also comprises a control unit 113 embodied to actuate the medical imaging device 101 based on the determined imaging parameter 4 for generating the second three-dimensional image dataset.

The data processing unit 115 and the control unit 113 can be implemented in the form of a computer, a microcontroller or an integrated switching circuit. The data processing unit 115 and the control unit 113 can comprise hardware elements or software elements, for example a microprocessor or a so-called FPGA (field programmable gate array). It can also entail a group of computers (another technical term for a real group is "cluster").

The apparatus can also include a storage unit 117. The storage unit 117 can also be included by the data processing unit. This can be implemented as a random-access memory (RAM for short) or as a permanent mass storage device (hard disk, USB stick, SD card, solid state disk). An interface 15 can be a hardware or software interface (for example PCI bus, USB or firewire). Herein, the storage unit 117 can, for example, be configured to buffer a first 3D image dataset for usage in accordance with the method according to an embodiment of the invention.

The apparatus preferably furthermore comprises at least one input unit and/or at least one output unit, which are not depicted here. An input unit and/or output unit enables, for example, manual interaction by a user, for example starting or stopping the method according to the invention, a confirmation or a correction by a user. An output unit in the form of a depiction unit can also enable the depiction of the first and/or second three-dimensional image dataset.

The subject matter of the invention is not restricted to the above-described example embodiments. Rather, further embodiments of the invention can be derived by the person skilled in the art from the above description. In particular, the individual features of the invention described on the basis of the different example embodiments and the embodiment variants thereof can also be combined in another way.

Although the invention has been illustrated and described in greater detail with reference to the referred example embodiments, the invention is not restricted thereby. Other variations and combinations can be derived herefrom by the person skilled in the art without departing from the essential concept of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for actuating a medical imaging device for generating a second three-dimensional image dataset including a target region in a region of interest of a patient with a functional impairment, the method comprising:
    providing, via at least one processor, a first three-dimensional image dataset including the region of interest of the patient;
    identifying, via the at least one processor, the target region based on the first three-dimensional image dataset, wherein a partial region of the region of interest with the functional impairment is determined;
    determining, via the at least one processor, an imaging parameter based on the target region, the imaging parameter for generating the second three-dimensional image dataset; and
    actuating, via a controller, the medical imaging device based on the imaging parameter for generating the second three-dimensional image dataset; wherein
    the imaging parameter includes a recording region for recording, via the medical imaging device, measurement data for generating the second three-dimensional image dataset, and
    the actuating includes positioning a measurement data recording device, of the medical imaging device, relative to the patient.

2. The method of claim 1, wherein
    the region of interest includes at least a part of a head of the patient, and
    the target region includes at least a part of a brain of the patient.

3. The method of claim 1, wherein
    the patient is a stroke patient, and
    the identifying identifies a part of a brain of the patient affected by an ischemic infarction as the partial region.

4. The method of claim 1, wherein the identifying identifies an ischemic core region.

5. The method of claim 1, wherein the identifying identifies the target region at least one of based on a segmentation algorithm, based on a threshold method or with aid of an anatomical atlas automatically.

6. The method of claim 1, wherein the identifying includes application of a trained function.

7. The method of claim 1, wherein the imaging parameter includes at least one of an image acquisition parameter for recording the measurement data for generating the second three-dimensional image dataset or an image reconstruction parameter for image reconstruction of the second three-dimensional image dataset.

8. The method of claim 1, wherein the imaging parameter includes the recording region and a reconstruction volume.

9. A method for actuating a medical imaging device for generating a second three-dimensional image dataset including a target region in a region of interest of a patient with a functional impairment, the method comprising:
    providing, via at least one processor, a first three-dimensional image dataset including the region of interest of the patient;
    identifying, via the at least one processor, the target region based on the first three-dimensional image dataset, wherein a partial region of the region of interest with the functional impairment is determined;
    determining, via the at least one processor, an imaging parameter based on the target region, the imaging parameter for generating the second three-dimensional image dataset; and
    actuating, via a controller, the medical imaging device based on the imaging parameter for generating the second three-dimensional image dataset; wherein
    the first three-dimensional image dataset is a native image dataset or an angiography image dataset, and
    the second three-dimensional image dataset is a perfusion image dataset.

10. The method of claim 1, wherein the first three-dimensional image dataset is a three-dimensional image dataset having a shortest time interval to time of provision, from among a plurality of first three-dimensional image datasets.

11. An apparatus to actuate a medical imaging device to generate a second three-dimensional image dataset including a target region in a region of interest of a patient with a functional impairment, the apparatus comprising:
    at least one processor configured to
        provide a first three-dimensional image dataset including the region of interest of the patient, identify the target region based on the first three-dimensional image dataset, wherein a partial region of the region of interest with the functional impairment is determined, and determine, based on the target region, an imaging parameter for generating the second three-dimensional image dataset; and a controller configured to actuate the medical imaging device based on the imaging parameter for generating the second three-dimensional image dataset; wherein the imaging parameter includes a recording region for recording, via the medical imaging device, measurement data for generating the second three-dimensional image dataset, and the controller is configured to position a measurement data recording device, of the medical imaging device, relative to the patient.

12. The apparatus of claim 11, wherein the medical imaging device is a computed tomography device.

13. A vehicle including the medical imaging device and the apparatus of claim 11.

14. The vehicle of claim 13, wherein the vehicle is an ambulance.

15. A non-transitory computer readable medium storing a computer program including program segments that, when executed by at least one processor, cause the at least one processor to perform the method for actuating the medical imaging device of claim 1.

16. The method of claim 2, wherein
the patient is a stroke patient, and
the identifying identifies a part of the brain of the patient, affected by an ischemic infarction, as the partial region.

17. The method of claim 2, wherein the identifying includes application of a trained function.

18. The method of claim 2, wherein the imaging parameter includes at least one of an image acquisition parameter for recording the measurement data for generating the second three-dimensional image dataset or an image reconstruction parameter for image reconstruction of the second three dimensional image dataset.

19. A non-transitory computer readable medium storing a computer program including program segments that, when executed by at least one processor, cause the at least one processor to execute the method for actuating the medical imaging device of claim 2.

* * * * *